United States Patent
Stüber et al.

(10) Patent No.: US 7,987,719 B2
(45) Date of Patent: Aug. 2, 2011

(54) DEVICE FOR THE ULTRASOUND TESTING OF HOT ROLLING MATERIAL

(75) Inventors: Axel Stüber, Osnabrück (DE); Peter Van Hüllen, Ibbenbühren (DE)

(73) Assignee: Georgsmarienhütte GmbH, Georgsmarienhütte (DE)

( * ) Notice: Subject to any disclaimer, the term of this patent is extended or adjusted under 35 U.S.C. 154(b) by 505 days.

(21) Appl. No.: 11/992,245

(22) PCT Filed: Jul. 27, 2006

(86) PCT No.: PCT/DE2006/001298
§ 371 (c)(1),
(2), (4) Date: May 20, 2008

(87) PCT Pub. No.: WO2007/033633
PCT Pub. Date: Mar. 29, 2007

(65) Prior Publication Data
US 2009/0260439 A1    Oct. 22, 2009

(30) Foreign Application Priority Data
Sep. 20, 2005    (DE) .......................... 10 2005 044 760

(51) Int. Cl.
*G01N 29/22* (2006.01)
(52) U.S. Cl. ................. 73/584; 73/599; 73/622; 73/639
(58) Field of Classification Search .................... 73/584, 73/599, 600, 618, 622, 639, 642, 644
See application file for complete search history.

(56) References Cited

U.S. PATENT DOCUMENTS

| | | | | |
|---|---|---|---|---|
| 3,423,993 | A | | 1/1969 | Lynnworth |
| 3,803,904 | A | * | 4/1974 | Diem et al. ...................... 73/640 |
| 4,160,387 | A | | 7/1979 | Ihara et al. |
| 5,535,628 | A | * | 7/1996 | Rutherford ..................... 73/622 |
| 6,341,525 | B1 | * | 1/2002 | Takada et al. .................. 73/627 |
| 6,666,094 | B1 | * | 12/2003 | Sauerland ....................... 73/618 |

(Continued)

FOREIGN PATENT DOCUMENTS

DE    16 48 652    6/1971

(Continued)

OTHER PUBLICATIONS

International Search Report.

(Continued)

*Primary Examiner* — Jacques M Saint Surin
(74) *Attorney, Agent, or Firm* — Collard & Roe, P.C.

(57) ABSTRACT

The invention relates to a device for the ultrasound testing of hot rolling material during the rolling procedure in one of a plurality of rolling stands in a rolling train which are arranged one behind the other, comprising at least two rolls which leave a roll gap between them, there being associated with the rolls ultrasound testing heads which are arranged such that parts of the roll body itself serve as the path along which the ultrasound waves pass on their way to the rolling material to be tested in the roll gap, which is characterised in that the rolls provided with the ultrasound testing heads are adjustable, have a straight transverse profile and a diameter which is a multiple of the width of the roll gap, with the result that a large rolling angle ($\alpha$) is provided, and these rolls are arranged in one of the first rolling stands of the rolling train.

9 Claims, 3 Drawing Sheets

U.S. PATENT DOCUMENTS

Figure 1:
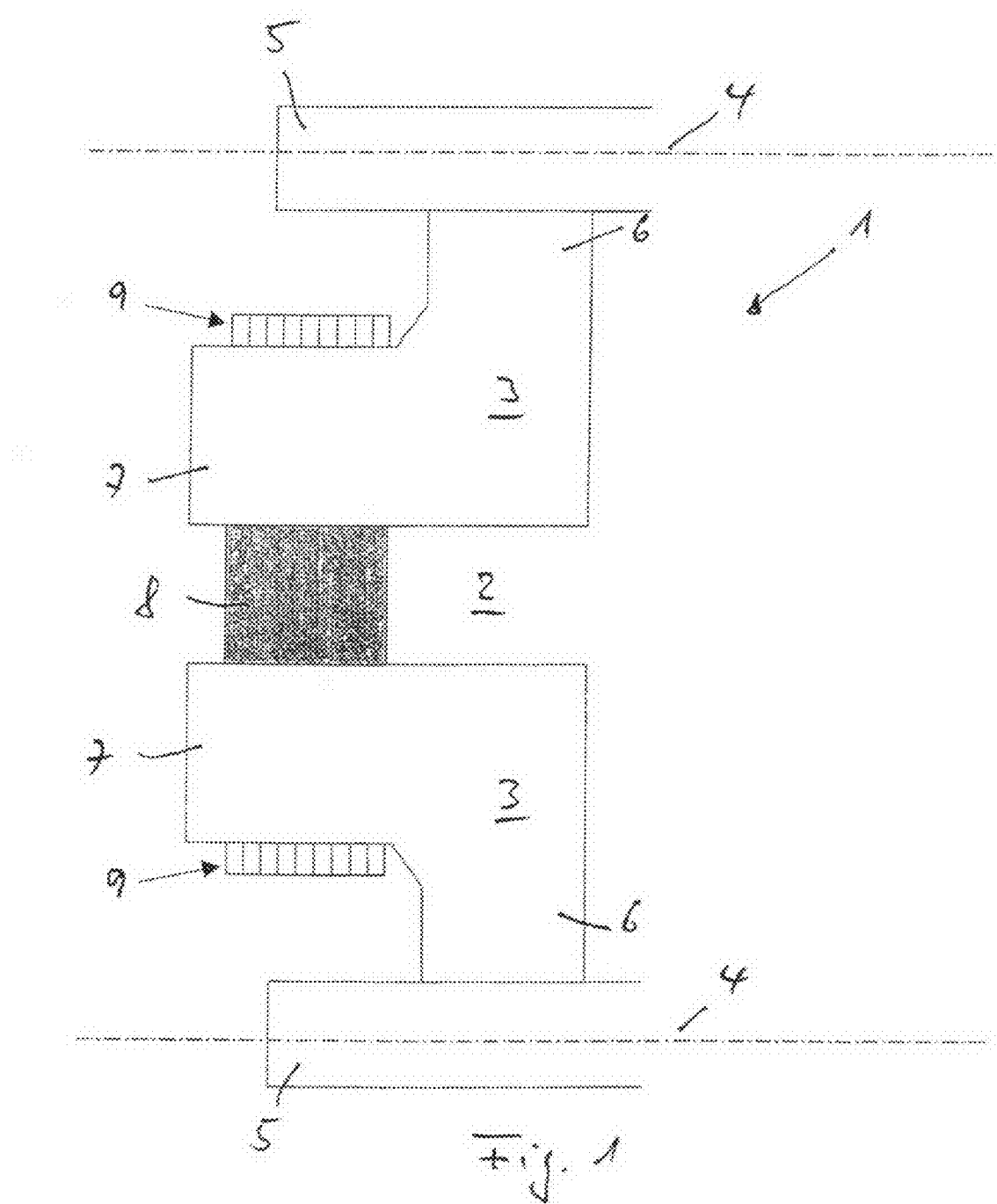

| | | | |
|---|---|---|---|
| 6,674,298 B2 * | 1/2004 | Felici et al. | 324/762 |
| 6,836,696 B2 | 12/2004 | Van Hullen | |
| 6,945,114 B2 * | 9/2005 | Kenderian et al. | 73/643 |
| 7,562,578 B2 * | 7/2009 | Figge | 73/639 |

FOREIGN PATENT DOCUMENTS

| | | | |
|---|---|---|---|
| DE | 199 15 203 | | 2/2000 |
| EP | 0 106 527 | | 4/1984 |
| JP | 08290217 | * | 11/1996 |
| WO | WO 01/96040 | | 12/2001 |

OTHER PUBLICATIONS

Fink, *"Moeglichkeiten zur Automatisierung der zerstoerungsfreien Pruefung von Warmwalzerzeugnissen im laufenden Betrieb,"* Stahl I. Eisen, Mar. 25, 1965, Duesseldorf, West Germany, vol. 85, No. 6, pp. 353-372. XP-008073950 (ISR) (English Abstract on first page).

* cited by examiner

DEVICE FOR THE ULTRASOUND TESTING OF HOT ROLLING MATERIAL

CROSS REFERENCE TO RELATED APPLICATIONS

Applicants claim priority under 35 U.S.C. §119 of German Application No. 10 2005 044 760.0 filed Sep. 20, 2005. Applicants also claim priority under 35 U.S.C. §365 of PCT/DE2006/001298 filed Jul. 27, 2006. The international application under PCT article 21(2) was not published in English.

The invention relates to a device for the ultrasound testing of hot rolling material during the rolling procedure in one of a plurality of rolling stands in a rolling train which are arranged one behind the other, comprising at least two rolls which leave a roll gap between them, there being associated with the rolls ultrasound testing heads which are arranged such that parts of the roll body itself serve as the path along which the ultrasound waves pass on their way to the rolling material to be tested in the roll gap.

A device of this kind is known for example from DE 199 15 203 C2. The device presented there is one in a rolling stand which is positioned upstream of the finishing stand in the rolling sequence. That means that at this point the steel is already almost completely rolled out into its desired form. As a result of this, it becomes more difficult to identify faults, for example inclusions, within the rolling material as a result of the elongation it has undergone. The reflective surface in the beam becomes smaller and smaller and the signal weaker and weaker.

In the embodiment which is specified as preferred in the published specification cited above, three rolls are provided arranged in a star shape (a so-called Kocks block) which form the roll gap between them. These disc-type rolls have to be manufactured or re-worked specially so that the ultrasound testing heads can be installed.

Because a rolling stand of this kind is—as stated above—a stand upstream of the finishing stand, in the event of differing dimensions for the stock different grooves have also to be provided, which entails considerable complexity for assembly and storage. The curvature of the grooves of the rolls is moreover disadvantageous because it ensures that the ultrasound beam is focused geometrically, although this is not always desirable. This focusing is aided by the ratios between the speeds of the sound waves. The bundling of the ultrasound beam means that the sound passes through the stock unevenly. This makes it necessary to increase the number of testing heads and to test at additional angles.

Moreover, the curvature also ensures that the energy of the ultrasound beam is scattered wherever the beam does not meet the groove in a perpendicular direction. These reflected portions may create problems in the testing, in the form of phantom echoes. In some cases, it is very difficult to suppress these if the relationships between the angles are unfavourable.

A further disadvantage is the small diameter of the rolls, which has a relatively pronounced defocusing effect on the ultrasound beam in the longitudinal direction. Here, the effect of the transition from testing head to roll body, ensured by coupling water, is crucial.

A further crucial disadvantage of the previously known device lies in the limitation on the testing dimensions. This means that the prepath in the roll through which the sound is passed has to be at least long enough for the time it takes to cover the prepath to be greater than that required for the stock to pass through at rapid speed.

The object of the invention is therefore to construct a device of the type mentioned above such that more reliable testing results can be achieved with substantially less complexity.

This object is achieved in accordance with the characterising part of Claim 1 in that the rolls provided with the ultrasound testing heads are adjustable, have a straight transverse profile and a diameter which is a multiple of the width of the roll gap, with the result that a large rolling angle ($.\alpha.$) is provided, and these rolls are arranged in one of the first rolling stands of the rolling train.

This means that testing is performed in a rolling stand at a relatively early stage in the rolling procedure, with the result that the elongation of the inclusions in the rolling material is relatively small but the shaping sufficient to break up the cast structure and compress porous areas. The cast structure has to be broken up so that ultrasound testing can be carried out at a frequency above 2 MHz. Only above this frequency can small inclusions be identified to a sufficient extent. The core of the stock has to be compressed to prevent the piece of stock concerned from being rejected, since ultrasound testing cannot distinguish between porous areas and inclusions.

As a result of the straight profile of the rolls, during the shaping procedure the profile of the rolling material also becomes square or rectangular, it being possible as a result of the large diameter of the rolls to provide a large shaping region and hence also a large region for exposure to sound waves. As a result of the large diameter, furthermore, the effect is that the defocusing is limited and the maximum energy can be introduced into the rolling material.

The rolling stand is set up such that it shapes to ensure sufficiently good contact between the rolls and the rolling material. The contact zone becomes larger as the degree of forming increases. This too contributes to making the energy introduced greater.

In a preferred embodiment, the rolls used are so-called cantilever rolls, in which the roll casing projects beyond the roll disc at least on one side. These cantilever rolls provide the advantages mentioned above of a large diameter and sufficient transmission of force.

Moreover, the shoulder-like projection of the roll casing provides an advantageous location for mounting the ultrasound testing heads, namely in accordance with Claim 3, on the side of the roll casing pointing towards the roll axis.

Unlike the prior art cited above, the rolls do not need to be re-worked or made specially, because with the cantilever rolls the arrangement of the ultrasound testing heads can readily be made flush with the rolling material.

Thus, the alignment of the ultrasound waves in a manner perpendicular to the rolling material surface in the roll gap (Claim 4) is possible without problems.

In accordance with Claim 6, as the ultrasound testing heads a plurality of conventional testing heads arranged in a line may be provided, aligned to meet the testing requirements by appropriate individual control.

In accordance with Claim 7, and advantageously, the use of so-called group emitters is therefore provided. The cantilever rolls which are preferred in accordance with the invention may be used over the entire range of dimensions of production, since they only have to be adjusted, with no need to use a new groove (see Claim 1). In particular, with group emitters and with clear guidance of the rolling material, the dimension of the stock can be taken into account by appropriate switching off and on within a line of group emitters. The crucial advantage of the group emitters lies in the possibility of pivoting the ultrasound beam in order to expose inclusions to sound waves in optimum manner, since these frequently have acoustically anisotropic properties. As a result of pivoting the acoustic beam, even inclusions close to the edge can be detected.

During testing, any conceivable modes of transmission and reception are possible. It is possible to operate either in a mode in which sound passes through, or with a method of echoing a transmitted pulse.

To ensure that the ultrasound only undergoes slight scattering and there is no attenuation of the returning signals, before testing a descaling is performed to remove the coarse scale that has built up after the roughing procedure.

The stock is fixed in a clearly defined position by rolling fittings or by rolling stands arranged upstream and downstream so that testing can be adjusted accordingly thereto.

Figure 2:
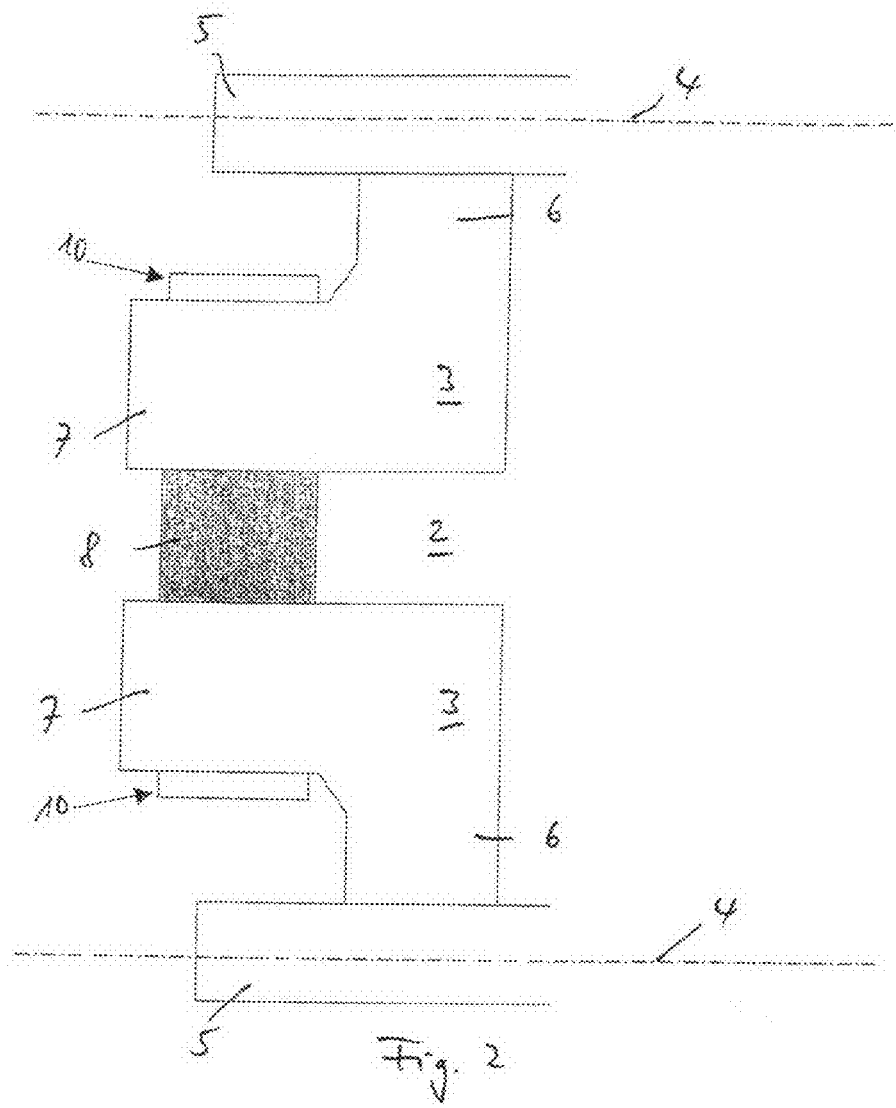
Figure 3:
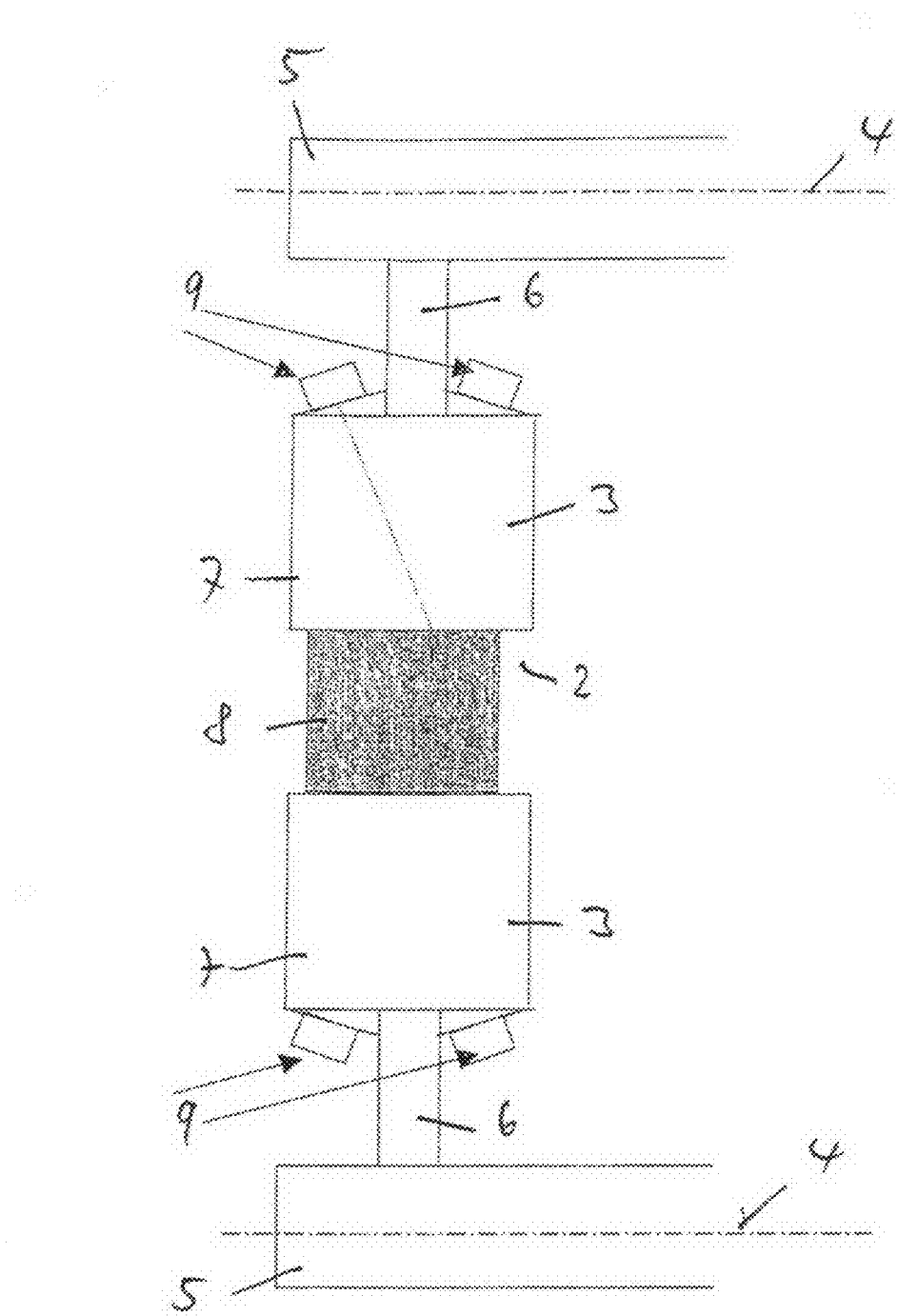

The invention will be explained below with reference to drawings, in which:

FIG. 1 shows a detail of a cantilever rolling stand with conventional ultrasound testing heads, FIG. 2 shows an illustration in accordance with FIG. 2 with group emitters as the testing heads, and FIG. 3 shows an alternative rolling stand with an alternative arrangement of testing heads.

In FIGS. 1 and 2, a detail of a rolling stand is illustrated, designated by the general reference numeral 1.

It substantially comprises two cantilever rolls 3 which leave a roll gap 2 between them and whereof the axis of rotation 4 is formed by the shaft 5. The rolls 3 each have a disc 6 and, projecting laterally outwards therefrom, an annular attached part 7. Between these two projecting regions 7 of the rolls 3 is the rolling material 8 to be tested.

On the side of the attached part 7 pointing towards the shaft 5, the actual testing device 9 is arranged flush with the roll gap 2 and the rolling material 8.

The case of FIG. 1 shows conventional ultrasound testing heads which are arranged in the manner of a matrix and are connected up such that they can be triggered individually, which has an effect on the direction in which sound is propagated and on the intensity.

In FIG. 2, all the elements in FIG. 1 have been given the same reference numerals. The only difference is that instead of the conventional ultrasound testing heads 9 in this case so-called group emitters 10 are provided. These group emitters have the advantage that the possibilities of triggering and testing are more versatile.

FIG. 3 illustrates an alternative arrangement of rolls in which the group emitters 9 are also arranged on the side of the attached part 7 pointing towards the axis 4.

Here, however, the ultrasound testing heads 9 are arranged such that, once that sound has passed through the attached part 7, they can pass sound obliquely through the rolling material 8. By triggering the testing heads 9 appropriately, however, it is also possible for sound to pass through in a perpendicular manner. This structure is intended to allow better scanning of the zone close to the surface.

Common to all the embodiments, however, is the fact that the testing surface can be presented in optimum manner by the geometry of the rolls, at a point in the rolling procedure at which the inclusions (that is to say, the faults to be identified within the rolling material) have not yet been elongated to any great extent and so give a clear signal when the sound passes through the rolling material.

The invention claimed is:

1. A rolling train having a plurality of rolling stands arranged one behind the other, each rolling stand comprising at least first and second rolls which leave a roll gap having a roll gap width between the first and second rolls, there being associated with each roll of at least one rolling stand a respective ultrasound testing head arranged such that parts of the roll body itself serve as a pass-through distance for the ultrasound waves to pass through to the rolled material to be tested in the roll gap, wherein the rolls provided with the ultrasound testing heads are useable for calibration of the roll gap width, have a straight transverse profile in the region of the roll gap and a diameter which is a multiple of the roll gap width, with the result that a large rolling angle is provided, the rolls provided with the ultrasonic testing heads being arranged in the at least one rolling stand of the rolling train at a location where the forming of the material to be tested is sufficient for resolution of the cast structure and compaction of porosities in the material but stretching of inclusions in the material is still slight.

2. The rolling train according to claim 1, wherein the rolls provided with the ultrasonic testing heads are cantilever rolls in which the roll surfaces have, at least on one side, an annular attached part which projects outwards from the disc.

3. The rolling train according to claim 2, wherein the ultrasound testing heads are arranged on the side of the annular attached part pointing towards the roll axis.

4. The rolling train according to claim 3, wherein the ultrasound waves are directed in a manner perpendicular to the rolled material surface in the roll gap.

5. The rolling train according to claim 4, wherein the ultrasound waves are directed obliquely towards the rolled material surface in the roll gap.

6. The rolling train according to claim 1, wherein a plurality of ultrasound testing heads are provided, wherein said plurality of ultrasonic testing heads are arranged in the manner of a matrix and connected to one another.

7. The rolling train according to claim 1, wherein group emitters are provided as the ultrasound testing heads.

8. The rolling train according to claim 1, wherein the rolled material to be tested is held by rolling fittings in a constant measuring position as the rolled material passes through.

9. The rolling train according to claim 1, wherein the rolled material to be tested is held in a constant measuring position as the rolled material passes through by rolling stands arranged upstream and/or downstream.

* * * * *